(12) United States Patent
Walker et al.

(10) Patent No.: US 6,498,020 B1
(45) Date of Patent: Dec. 24, 2002

(54) FUSION PROTEINS COMPRISING COILED-COIL STRUCTURES DERIVED OF BOVINE $IF_1$ ATPASE INHIBITOR PROTEIN

(75) Inventors: John Walker, Cambridge (GB); Bruno Miroux, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/464,152

(22) Filed: Dec. 27, 1999

Related U.S. Application Data

(63) Continuation of application No. PCT/GB98/02041, filed on Jul. 10, 1998.

(30) Foreign Application Priority Data

Jul. 11, 1997 (GB) ............................................. 9714680

(51) Int. Cl.$^7$ ........................... C12P 21/06; C12P 21/04; A61K 39/00; C07K 17/00
(52) U.S. Cl. .................. 435/69.1; 435/69.7; 424/184.1; 424/185.1; 530/350; 530/412; 530/413
(58) Field of Search ................................. 530/350, 412, 530/413; 435/69.7, 7.1; 424/184.1, 185.1

(56) References Cited

FOREIGN PATENT DOCUMENTS

WO     WO 97/12988     4/1997

OTHER PUBLICATIONS

International Search Report PCT/GB 98/02041.

Van Raaij, et al., The ATPase Inhibitor Protein from Bovine Heart Mitochondria: The Minimal Inhibitory Sequence, *Biochemistry*, vol. 35, 1996, pp. 15618–15625.

Wolber, et al., A Universal Expression–Purification System Based on the Coiled–Coil Interaction of Myosin Heavy Chain, *Bio/Technology vol. 10*, 1992, pp. 900–904.

Tripet, et al., Engineering a *de novo*–designed Coiled–coil Heterodimerization Domain for the Rapid Detection, Purification and Characterization of Recombinantly Expressed Peptides and Proteins, *Protein Engineering*, vol. 9, 1996, pp. 1029–1042.

*Primary Examiner*—Anne M. Wehbe'
*Assistant Examiner*—Q. Janice Li
(74) *Attorney, Agent, or Firm*—Kathleen M. Williams; Palmar & Dodge, LLP

(57) ABSTRACT

The present invention relates to a fusion protein comprising a first amino acid sequence comprising the sequence of the C-terminal 40 amino acids of bovine $IF_1$ ATPase inhibitor protein, and a second amino acid sequence not naturally associated with the first region. The invention further relates to methods for preparing an immunoglobulin comprising immunizing an animal with the fusion protein and recovering immunoglobulin specific for a region of the fusion protein.

9 Claims, No Drawings

SEQUENCE LISTING

```
<160> NUMBER OF SEQ ID NOS: 25

<210> SEQ ID NO 1
<211> LENGTH: 141
<212> TYPE: DNA
<213> ORGANISM: Bos bovis
<220> FEATURE:
<221> NAME/KEY: CDS
<222> LOCATION: (1)..(141)
<223> OTHER INFORMATION:

<400> SEQUENCE: 1 atg gcc ttg aag aaa cac cat gaa aat gag atc tct cat cat gca aag        48
Met Ala Leu Lys Lys His His Glu Asn Glu Ile Ser His His Ala Lys
1               5                   10                  15 gag att gag cgc ctg cag aaa gaa att gag cgg cat aag cag tcg atc        96
Glu Ile Glu Arg Leu Gln Lys Glu Ile Glu Arg His Lys Gln Ser Ile
            20                  25                  30 aag aaa cta aaa cag agt gag gat gac gac gga tcc ccg aag ctt          141
Lys Lys Leu Lys Gln Ser Glu Asp Asp Asp Gly Ser Pro Lys Leu
        35                  40                  45

<210> SEQ ID NO 2
<211> LENGTH: 47
<212> TYPE: PRT
<213> ORGANISM: Bos bovis

<400> SEQUENCE: 2

Met Ala Leu Lys Lys His His Glu Asn Glu Ile Ser His His Ala Lys
1               5                   10                  15

Glu Ile Glu Arg Leu Gln Lys Glu Ile Glu Arg His Lys Gln Ser Ile
            20                  25                  30

Lys Lys Leu Lys Gln Ser Glu Asp Asp Asp Gly Ser Pro Lys Leu
        35                  40                  45

<210> SEQ ID NO 3
<211> LENGTH: 13
<212> TYPE: DNA
<213> ORGANISM: Artificial sequence
<220> FEATURE:
<223> OTHER INFORMATION: filtering sequence
<220> FEATURE:
<221> NAME/KEY: misc_feature
<222> LOCATION: (1)..(13)
<223> OTHER INFORMATION: N = substitution by filtering program for
      low-complexity sequence

<400> SEQUENCE: 3
nnnnnnnnnn nnn                                                          13
```

```
<210> SEQ ID NO 4
<211> LENGTH: 9
<212> TYPE: PRT
<213> ORGANISM: Artificial sequence
<220> FEATURE:
<223> OTHER INFORMATION: filtering sequence
<220> FEATURE:
<221> NAME/KEY: MISC_FEATURE
<222> LOCATION: (1)..(9)
<223> OTHER INFORMATION: X = substitution by filtering program for
      low-complexity sequence

<400> SEQUENCE: 4

Xaa Xaa Xaa Xaa Xaa Xaa Xaa Xaa Xaa
1               5

<210> SEQ ID NO 5
<211> LENGTH: 4
<212> TYPE: PRT
<213> ORGANISM: Artificial sequence
<220> FEATURE:
<223> OTHER INFORMATION: protease cleavage region for Factor Xa

<400> SEQUENCE: 5

Ile Glu Gly Arg
1

<210> SEQ ID NO 6
<211> LENGTH: 5
<212> TYPE: PRT
<213> ORGANISM: Artificial Sequence
<220> FEATURE:
<223> OTHER INFORMATION: protease cleavage region targeted by
      Enterokinase

<400> SEQUENCE: 6

Asp Asp Asp Asp Lys
1               5

<210> SEQ ID NO 7
<211> LENGTH: 5
<212> TYPE: PRT
<213> ORGANISM: Artificial Sequence
<220> FEATURE:
<223> OTHER INFORMATION: protease cleavage region targeted by thrombin

<400> SEQUENCE: 7

Leu Val Pro Arg Gly
1               5

<210> SEQ ID NO 8
<211> LENGTH: 5
<212> TYPE: PRT
<213> ORGANISM: Artificial Sequence
<220> FEATURE:
<223> OTHER INFORMATION: cleavable linker

<400> SEQUENCE: 8

Gly Ser Pro Lys Leu
1               5

<210> SEQ ID NO 9
<211> LENGTH: 6
<212> TYPE: PRT
<213> ORGANISM: Artificial sequence
<220> FEATURE:
<223> OTHER INFORMATION: linker cleavable by Factor Xa
```

```
<400> SEQUENCE: 9

Gly Ser Ile Glu Gly Arg
1               5

<210> SEQ ID NO 11
<211> LENGTH: 11
<212> TYPE: PRT
<213> ORGANISM: Artificial sequence
<220> FEATURE:
<223> OTHER INFORMATION: linker cleavable by thrombin

<400> SEQUENCE: 10

Gly Ser Ser Leu Val Pro Arg Gly Ser Gly Ser
1               5                   10

<210> SEQ ID NO 11
<211> LENGTH: 6
<212> TYPE: PRT
<213> ORGANISM: Artificial sequence
<220> FEATURE:
<223> OTHER INFORMATION: linker

<400> SEQUENCE: 11

Gly Ser Lys Asn Val Met
1               5

<210> SEQ ID NO 12
<211> LENGTH: 2
<212> TYPE: PRT
<213> ORGANISM: Artificial sequence
<220> FEATURE:
<223> OTHER INFORMATION: linker

<400> SEQUENCE: 12

Gly Ser
1

<210> SEQ ID NO 13
<211> LENGTH: 6
<212> TYPE: PRT
<213> ORGANISM: Artificial sequence
<220> FEATURE:
<223> OTHER INFORMATION: linker

<400> SEQUENCE: 13

Gly Ser Pro Lys Leu Met
1               5

<210> SEQ ID NO 14
<211> LENGTH: 8
<212> TYPE: PRT
<213> ORGANISM: Artificial sequence
<220> FEATURE:
<223> OTHER INFORMATION: Histidine tag

<400> SEQUENCE: 14

Glu Phe His His His His His His
1               5

<210> SEQ ID NO 15
<211> LENGTH: 54
<212> TYPE: PRT
<213> ORGANISM: Artificial sequence
<220> FEATURE:
<223> OTHER INFORMATION: Random Peptide

<400> SEQUENCE: 15
```

Gly Ser Ser Leu Ser Ile Trp Trp Leu Leu Thr Cys Ile Arg Ser Pro
1               5                   10                  15

Arg Pro Trp Pro Val Lys Val Ala Arg Trp Lys Met Arg Leu Arg Thr
                20                  25                  30

Ser Ile Ser Ala Ala Gln Glu Trp Cys Ala Pro Pro Arg Thr Ile
            35                  40                  45

Lys Met Ser Gln Ser Trp
    50

<210> SEQ ID NO 16
<211> LENGTH: 39
<212> TYPE: PRT
<213> ORGANISM: Artificial sequence
<220> FEATURE:
<223> OTHER INFORMATION: Random Peptide

<400> SEQUENCE: 16

Gly Ser Gly Pro Gln Pro Ala Trp Arg Asn Asn Lys Thr Gly Thr Ala
1               5                   10                  15

Glu Trp Gly Arg Ile Asn Arg Arg Leu Asp Ala Ile Asn Val Ser Gly
                20                  25                  30

Thr Gly Ser Arg Thr Ala Asn
        35

<210> SEQ ID NO 17
<211> LENGTH: 22
<212> TYPE: PRT
<213> ORGANISM: Artificial Sequence
<220> FEATURE:
<223> OTHER INFORMATION: Random Peptide

<400> SEQUENCE: 17

Gly Ser Asn Cys Phe Phe Ser Pro Ser Ser Asn Ala His Ala Leu Pro
1               5                   10                  15

Cys Ser Ser Leu Leu Gln
            20

<210> SEQ ID NO 18
<211> LENGTH: 12
<212> TYPE: PRT
<213> ORGANISM: Artificial Sequence
<220> FEATURE:
<223> OTHER INFORMATION: Random Peptide

<400> SEQUENCE: 18

Gly Ser Pro Ser Val Met Arg Thr Arg Val Thr Arg
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Random Peptide

<400> SEQUENCE: 19

Gly Ser His Ala His Cys
1               5

<210> SEQ ID NO 20
<211> LENGTH: 9
<212> TYPE: PRT
<213> ORGANISM: Artificial sequence

```
<220> FEATURE:
<223> OTHER INFORMATION: Random Peptide

<400> SEQUENCE: 20

Gly Ser Leu Ser Leu Pro Phe Ala Arg
1               5

<210> SEQ ID NO 21
<211> LENGTH: 15
<212> TYPE: PRT
<213> ORGANISM: Artificial Sequence
<220> FEATURE:
<223> OTHER INFORMATION: Random Peptide

<400> SEQUENCE: 21

Gly Ser Leu Arg Cys Phe Ala Arg Ser Arg Ser Ser Gly Arg Cys
1               5                   10                  15

<210> SEQ ID NO 22
<211> LENGTH: 13
<212> TYPE: PRT
<213> ORGANISM: Artificial Sequence
<220> FEATURE:
<223> OTHER INFORMATION: Random Peptide

<400> SEQUENCE: 22

Gly Ser Pro Pro Arg Val Ala Ala Thr Val Glu Arg His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Random Peptide

<400> SEQUENCE: 23

Gly Ser Cys Ala Gly Cys Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Random Peptide

<400> SEQUENCE: 24

Gly Ser Arg Tyr
1

<210> SEQ ID NO 25
<211> LENGTH: 12
<212> TYPE: PRT
<213> ORGANISM: Artificial Sequence
<220> FEATURE:
<223> OTHER INFORMATION: Random Peptide

<400> SEQUENCE: 25

Gly Ser Arg Thr Asp Glu Thr Tyr Tyr Pro Ala Asp
1               5                   10
```

FUSION PROTEINS COMPRISING COILED-COIL STRUCTURES DERIVED OF BOVINE IF$_1$ ATPASE INHIBITOR PROTEIN

This application is a continuation of application Ser. No. PCT/GB98/02041, filed Jul. 10, 1998, which claims priority to application serial number GB61971460.7, filed Jul. 11, 1997. Both priority applications are incorporated herein by reference in their entirety.

The present invention relates to novel fusion partners for recombinantly-produced proteins. In particular, the invention relates to a polypeptide which is resistant to proteolytic degradation and capable of acting as a carrier to increase the immunogenicity of a protein fused to it.

Recombinant DNA technology has allowed industry to produce many proteins of commercial importance. Proteins are produced in a wide variety of expression systems which are based on, for example, bacterial, yeast, insect, plant and mammalian cells. one of the problems associated with the production of proteins by recombinant means is that host cells contain enzymes which degrade proteins and the presence of such enzymes present particular difficulties in the production of small polypeptides.

One approach to overcoming such difficulties is to express a recombinant protein of interest in the form of a fusion protein. DNA encoding the protein of interest is fused in-frame to a fusion partner protein and the resulting fusion is expressed. Often, a linker sequence encoding a protease cleavage sited between the two parts of the fusion is included to allow cleavage of the fusion after it has been recovered from its host cell.

The fusion partner protein is often one which may be recovered and purified by some form of highly specific affinity purification means. Examples of such proteins are well known in the art and include, for example, glutathione-S-transferase, maltose binding protein and β-lactamase.

However these fusion partner proteins are all relatively large and thus have a number of disadvantages. For example, it is essential to remove them before any meaningful procedure may be carried out on the protein of interest, since they are too large to enable it to function with any degree of independence. Many small polypeptides are still thus made by chemical synthesis.

The present invention arose in the course of our investigations into the structure of a bovine ATPase inhibitor protein, IFS. This is a small—84 amino acid—protein which helps to regulate the activity of ATP synthase in mitochondria.

SUMMARY OF THE INVENTION

We have expressed in *E. coli* a number of fusion proteins which comprise the foregoing region of bovine IF$_1$ ATPase inhibitor protein and a short sequence of a second protein. We have found that these fusion proteins can be expressed at high levels and isolated in intact form, from which the second protein may efficiently be recovered. The use of the C-terminal 40 amino acids as a fusion partner protein in a recombinant expression system thus allows expression of a desired polypeptide in a manner which protects the polypeptide from degradation in the host cell.

Thus the present invention provides a fusion protein comprising:
a) a first region comprising the sequence of the C-terminal 40 amino acids of bovine IF$_1$ ATPase inhibitor protein, or a derivative thereof; and
b) a second region not naturally associated with the first region comprising a polypeptide sequence of interest.

The first region may be located either N-terminal to or C-terminal to the second region. However it is preferred that it is located N-terminal to the second region, and most preferably it is at the N-terminus of the fusion protein. Preferably, the fusion protein further comprises a cleavable linker region between the first and second regions.

The invention further comprises a nucleic acid encoding the fusion protein of the invention, and preferably the nucleic acid forms part of an expression vector comprising the nucleic acid operably linked to a promoter.

The invention further comprises a host cell carrying the expression vector of the invention, and a method of preparing the fusion protein of the invention comprising (i) culturing the host cell under conditions which provide for the expression of the fusion protein from the expression vector within the host cell; and (ii) recovering the fusion protein from the cell.

In cases where the fusion protein further comprises a protease cleavable linker region between the first and second regions the method optionally further comprises cleaving the protein at the protease cleavable linker and recovering the second region.

DETAILED DESCRIPTION OF THE INVENTION

A: First Region

The first region of the fusion protein of the invention may comprise any natural or synthetic polypeptide comprising the sequence of bovine IF$_1$ ATPase inhibitor or a derivative thereof. Preferably, the first region has the sequence of the C-terminal 40 amino acids of bovine IF$_1$ ATPase inhibitor or a derivative thereof. A derivative, as defined herein, is a fragment, mutant or other derivative which retains a common structural determinant of the C-terminal 40 amino acids of bovine IF$_1$ ATPase inhibitor.

"Common structural determinant" means that the derivative in question at least one structural feature of the C-terminal 40 amino acids of bovine IF$_1$ ATPase inhibitor. In the following, references to "bovine IF$_1$ ATPase inhibitor" are to be understood as encompassing references to the C-terminal 40 amino acids of this protein, unless otherwise provided for.

Structural features includes possession of an epitope or antigenic site that is capable of cross-reacting with antibodies raised against a naturally occurring or denatured bovine IF$_1$ ATPase inhibitor polypeptide or a fragment thereof, possession of amino acid sequence identity with bovine IF$_1$ ATPase inhibitor and features having common a structure/function relationship. Thus the fusion partner provided by the present invention includes splice variants encoded by mRNA generated by alternative splicing of a primary transcript, amino acid mutant s, glycosylation variants and other co valent derivatives of bovine IF$_1$ ATPase inhibitor which retain the physiological and/or physical properties of bovine IF$_1$ ATPase inhibitor. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of bovine IF$_1$ ATPase inhibitor found with a particular species, preferably a mammal. Such a variant may be encoded by a related gene of the same gene family, by an allelic variant of a particular gene, or represent an alternative splicing variant of the bovine IF$_1$ ATPase inhibitor gene.

Derivatives which retain common structural features can be fragments of bovine IF$_1$ ATPase inhibitor. Fragments of bovine $IF_1$ ATPase inhibitor comprise individual domains thereof, as well as smaller polypeptides derived from the domains. Preferably, smaller polypeptides derived from bovine $IF_1$ ATPase inhibitor according to the invention define a single feature which is characteristic of bovine $IF_1$ ATPase inhibitor. Fragments may in theory be almost any size, as long as they retain the advantageous feature of bovine $IF_1$ ATPase inhibitor described herein.

Derivatives of bovine $IF_1$ ATPase inhibitor also comprise mutants thereof, which may contain amino acid deletions, additions or substitutions, subject to the requirement to maintain the characteristic feature of bovine $IF_1$ ATPase inhibitor described herein. Thus, conservative amino acid substitutions may be made substantially without altering the nature of bovine $IF_1$ ATPase inhibitor, as may truncations from the 5' or 3' ends. Deletions and substitutions may moreover be made to the fragments of bovine $IF_1$ ATPase inhibitor comprised by the invention. bovine $IF_1$ ATPase inhibitor mutants may be produced from a DNA encoding bovine $IF_1$ ATPase inhibitor which has been subjected to in vitro mutagenesis resulting e.g. in an addition, exchange and/or deletion of one or more amino acids. For example, substitutional, deletional or insertional variants of bovine $IF_1$ ATPase inhibitor can be prepared by recombinant methods and screened for immuno-crossreactivity with the native forms of bovine $IF_1$ ATPase inhibitor.

The fragments, mutants and other derivative of bovine $IF_1$ ATPase inhibitor preferably retain substantial homology with bovine $IF_1$ ATPase inhibitor. As used herein, "homology" means that the two entities share sufficient characteristics for the skilled person to determine that they are similar in origin and function. Preferably, homology is used to refer to sequence identity. Thus, the derivatives of bovine $IF_1$ ATPase inhibitor preferably retain substantial sequence identity with the sequence of SEQ ID No. 2.

"Substantial homology", where homology indicates sequence identity, means more than 50% sequence identity, preferably more than 75% sequence identity and most preferably a sequence identity of 90% or more, as judged by direct sequence alignment and comparison.

"Sequence homology", (or identity) may moreover be determined using any suitable homology algorithm, using for example default parameters. Advantageously, the BLAST algorithm is employed, with parameters set to default values. The BLAST algorithm is described in detail at the world wide web site ("www") for the National Center for Biotechnology Information (".ncbi") of the National Institutes of Health (".nih") of the U.S. government (".gov"), in the "/BLAST/" directory. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul with a few enhancements. The BLAST programs were tailored for sequence similarity searching, for example to identify homologues to a query sentence. The programs are not generally useful for motif-style searching. For a discussion of basic issues in similarity searching of sequence databases, see Atschul et al. (1994) Nature Genetics 6:119–129.

The five BLAST programs available perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX. TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is subsituted using the letter "N" in nucleotide sequence (e.g., "NNNNNNNNNNNNN" (SEQ ID NO:3)) and the letter "X" in protein sequences (e.g., "XXXXXXXXX" (SEQ ID NO:4)).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect. NCBI-gi Causes NCBI gi identifiers to be shown in the output, in addition to the accession and or locus name.

Most preferably, sequence comparisons are conducted using the simple BLAST search algorithm provided at the world wide web site ("www") for the National Center for Biotechnology Information (".ncbi") of the National Institutes of Health (".nih") of the U.S. government (".gov"), in the "/BLAST/" directory.

Advantageously, the first region comprises the sequence set forth in SEQ. ID. No. 1.

In addition synthetic variants of such dequences or regions thereof may be used provided that they retain the ability to form effective fusion partners.

Synthetic variants may be made by standard recombinant DNA techniques. For example, site-directed mutagenesis may be used to introduce changes to the coding region of the DNA of SEQ. ID. No. 1. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

It is desirable to keep the size of the first region in proportion to the overall size of the fusion protein. This can be especially important where in structural determination of proteins by NMR it is often necessary to carry out isotopic labelling with $^{15}N$ or $^{13}C$. This is expensive and with a long fusion partner much of the incorporated radioactivity is removed when the carrier protein (e.g. GST in many cases) is cleaved off. Thus the fusion partner may be between 25 and 100 amino acids in size.

The ability of a sequence according to the invention to function as a fusion partner as detailed herein can be determined empirically, for example using the methods set forth herein.

B: Second Region

The second region of the fusion protein according to the invention may comprise any polypeptide sequence of interest which is not naturally associated with the first region. Usually this will mean that the sequence of interest will be found in nature encoded by a gene different from the gene encoding the first region. This may be determined easily by examining the sequences of the first and second regions against publicly available sequence databanks. The second region may be from the same species as the first region, or from a different species. It is also possible that the first and second regions are derived from portions of the same protein but are present in the fusion protein of the invention in a manner different from the natural protein sequence.

The fusion protein according to the invention may be of any size although in general the invention is particularly useful when the polypeptide sequence of interest is short, e.g. from 2 ;to 100 amino acids in length, preferably 2 to 50 or even 2 to 30 or 5 to 10 amino acids in size. However larger polypeptide sequences of interest, e.g. up 150, 200, 400 or 1000 amino acids are also contemplated. The invention is particularly advantageous for the preparation of small polypeptides which are currently difficult to manufacture by recombinant means. Examples of such polypeptides include fragments of chaperone proteins, metabolic enzymes, DNA and RNA binding proteins, antibodies, viral proteins, intrinsic membrane proteins (including transport proteins from mitochondria, seven-helix receptor molecules, T-cell receptors), and cytoskeletal complexes, antibody binding peptides, peptide hormones (and other biologically active peptides made by ribosomal synthesis), and small subunits from multi-subunit biological structures such as respiratory enzymes, the ATP synthase. In general, the invention is suitable for use with peptides of any dimension, but the advantageous properties thereof are best exploited with small polypeptides, for example from 2 to 50 amino acids in length, particularly from 2 to 20 amino acids in length, and preferably from 5 to 10 amino acids in length.

A particular advantage of the present invention is that peptides may be produced by recombinant DNA technology which are so short that they would previously have been made by oligopeptide synthesis techniques. Thus it is possible to produce libraries of peptides, for example of mutants of biologically active peptides, which may be screened or otherwise analysed, cheaply and efficiently in recombinant expression systems, particularly bacterial expression systems.

C: Cleavable Linker Region

Where the first and second regions are linked by a cleavable linker region this may be any region suitable for this purpose. Preferably, the cleavable linker region is a protease cleavable linker, although other linkers, cleavable for example by small molecules, may be used. These include Met-X sites, cleavable by cyanogen bromide, Asn-Gly, cleavable by hydroxylamine, Asp-Pro, cleavable by weak acid and Trp-X celavable by, inter alia, NBS-skatole. Protease cleavage sites are preferred due to the milder cleavage conditions necessary and are found in, for example, factor Xa, thrombin and collagenase. Any of these may be used. The precise sequences are available in the art and the skilled person will have no difficulty in selecting a suitable cleavage site. By way of example, the protease cleavage region targeted by Factor Xa is I E G R (SEQ ID NO:5). The protease cleavage region targeted by Enterokinase is D D D D K (SEQ ID NO:6). The protease cleavage region targeted by Thrombin is L V P R G (SEQ ID NO:7).

D. Nucleic Acids

The invention also provides nucleic acid encoding the fusion proteins of the invention. These may be constructed using standard recombinant DNA methodologies. The nucleic acid may be RNA or DNA and is preferably DNA. Where it is RNA, manipulations may be performed via cDNA intermediates. Generally, a nucleic acid sequence encoding the first region will be prepared and suitable restriction sites provided at the 5' and/or 3' ends. Conveniently the sequence is manipulated in a standard laboratory vector, such as a plasmid vector based on pBR322 or pUC19 (see below). Reference may be made to Molecular Cloning by Sambrook et al. (Cold Spring Harbor, 1989) or similar standard reference books for exact details of the appropriate techniques.

Nucleic acid encoding the second region may likewise be provided in a similar vector system. Sources of nucleic acid may be ascertained by reference to published literature or databanks such as Genbank.

Nucleic acid encoding the desired first or second region may be obtained from academic or commercial sources where such sources are willing to provide the material or by synthesising or cloning the appropriate sequence where only the sequence data are available. Generally this may be done by reference to literature sources which describe the cloning of the gene in question.

Alternatively, where limited sequence data are available or where it is desired to express a nucleic acid homologous or otherwise related to a known nucleic acid, exemplary nucleic acids can be characterised as those nucleotide sequences which hybridise to the nucleic acid sequences known in the art.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68 ° C. High stringency conditions can be provided, for example, by hybridisation in an aqueous solution containing 6×SSC, 5×Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, nucleic acids suitable for forming the first or second region of a fusion protein according to the invention are obtainable according to methods well known in the art. For example, a DNA of the invention is obtainable by chemical synthesis, using polymerase chain reaction (PCR) or by screening a genomic library or a suitable cDNA library prepared from a source believed to possess the desired nucleic acid and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding the desired region of the fusion protein is to use PCR technology as described e.g. in section 14 of Sambrook et al., 1989. This method requires the use of oligonucleotide probes that will hybridise to the desired nucleic acid. Strategies for selection of oligonucleotides are described below..

Libraries are screened with probes or analytical tools designed to identify the gene of interest or the protein encoded by it. For cDNA expression libraries suitable means include monoclonal or polyclonal antibodies that recognise and specifically bind to the desired protein; oligonucleotides of about 20 to 80 bases in length that encode known or suspected cDNA encoding the desired protein from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding the desired protein may be isolated by screening suitable cDNA or genomic libraries under suitable hybridisation conditions with a probe.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases from a known or desired sequence. The nucleic acid sequences selected as probes should be of sufficient length and sufficiently unambiguous so that false positive results are minimised. The nucleotide sequences are usually based on conserved or highly homologous nucleotide sequences or regions of the desired protein. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein as SEQ. ID. No. 1 or fragments thereof can be used as probes, especially for isolating first region-encoding genes. Preferably, nucleic acid probes of the invention are labelled with suitable label means for ready detection upon hybridisation. For example, a suitable label means is a radiolabel. The preferred method of labelling a DNA fragment is by incorporating $\alpha^{32}$P DATP with the Klenow fragment of DNA polymerase in a random priming reaction, as is well known in the art. Oligonucleotides are usually end-labelled with $\gamma^{32}$P-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire desired sequence or a suitable oligonucleotide based on a portion of said DNA, positive clones are identified by detecting a hybridisation signal; the identified clones are characterised by restriction enzyme mapping and/or DNA sequence analysis, and then examined to ascertain whether they include DNA encoding a complete polypeptide (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce a mutant that has an amino acid sequence differing from the sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

The foregoing methods may, of course, be applied to the identification and modification or generation of sequences useful in any part of the fusion protein of the invention. In particular, the sequence of the $IF_1$ polypeptide C-terminal 40 amino acids provided herein as SEQ. ID. No. 1, or suitable fragments thereof as discussed above, may be used as a probe for the identification of further suitable sequences.

The first or second region may also be manipulated to introduce an appropriate restriction enzyme site at the terminus which is to be linked to the nucleic acid encoding the first region via a corresponding restriction enzyme site. Desirably the sites will be either the same or at least have matching cohesive ends. Of course, the first and second regions may be joined by alternative means; for example, first region may be incorporated into primers used to isolate or replicate the second region.

Where a protease cleavable linker region is required, this maybe introduced into the linked first and second regions (e.g. into the restriction site linking the two) or introduced into one or the other prior to their combination.

E. Expression Vectors and Host Cells

The nucleic acid encoding a fusion protein according to the invention, or constituent part(s) thereof. can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequences that enable the vector to replicate in one or more selected host cells. Typically in cloning vectors, these sequences enable the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the $2\mu$ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another organism for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding the fusion protein of the invention is more complex than that of exogenously replicated vector because restriction enzyme digestion is required to excise the DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript® vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up vector nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted;to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the fusion protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to the fusion-protein encoding nucleic acid. Such a promoter may be inducible or constitutive. The promoters are operably linked to DNA encoding the fusion protein by removing the promoter from the source DNA by restriction enzyme digestion and inserting the isolated promoter sequence into the vector. Both the native promoter sequence of one of the constituents of the fusion protein and many heterologous promoters may be used to direct amplification and/or expression of the DNA. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding the fusion protein using linkers or adaptors to supply any required restriction sites. Promoters for use in bacterial systems will also generally contain a Shine-Delgarno sequence operably linked to the DNA encoding the fusion protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for overproduction of many globular proteins, but in many other cases significant over-production cannot be achieved because of the toxicity of over-expression (Studier et al., 1990; George et al, J. Mol. Biol. 235; 424–435, 1994). Alternatively the polymerase gene may be introduced on a lambda phage by infection with an int- phage such as the CE6 phage which is commercially available (Novagen, Madison, USA). other vectors include vectors containing the lambda PL promoter such as PLEX (Invitrogen, NL) , vectors containing the trc promoters such as pTrcHisXpressTm (Invitrogen) or pTrc99 (Pharmacia Biotech, SE), or vectors containing the tac promoter such as pKK223-3 (Pharmacia Biotech) or PMAL (New England Biolabs, Mass., USA).

Moreover, the fusion protein gene according to the invention may include a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PHO5) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PHO5 gene and downstream promoter elements including a functional TATA box of the yeast GAP gene (PHO5-GAP hybrid promoter). A suitable constitutive PHO5 promoter is e.g. a shortened acid phosphatase PHO5 promoter devoid of the upstream regulatory elements (UAS) such as the PHO5 (-173) promoter element starting at nucleotide -173 and ending at nucleotide -9 of the PH50 gene.

Fusion protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with the gene encoding a component of the fusion protein, provided such promoters are compatible with the host cell systems.

Transcription of a DNA encoding the fusion protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to the coding sequence, but is preferably located at a site 5' from the promoter.

Advantageously, a eukaryotic expression vector encoding the fusion protein may comprise a locus control region (LCR). LCRs are capable of directing high-level integration site independent expression of transgenes integrated into host cell chromatin, which is of importance especially where the fusion protein gene is to be expressed in the context of a permanently-transfected eukaryotic cell line in which chromosomal integration of the vector has occurred, in vectors designed for gene therapy applications or in transgenic animals.

An expression vector includes any vector capable of expressing nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding the fusion protein according to the invention may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding the fusion protein in mammalian cells. Transient expression usually involves the use of an expression vector that is able to replicate efficiently in a host cell, such that the host cell accumulates many copies of the expression vector, and, in turn, synthesises high levels of fusion protein. For the purposes of the present invention, transient expression systems are useful e.g. for identifying fusion protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein. Those skilled in the art will readily envisage how these methods may be modified, if desired.

The invention moreover provides an expression vector comprising a first nucleic acid sequence encoding a polypeptide comprising the 40 C-terminal amino acids of bovine $IF_1$ ATPase inhibitor or a derivative thereof operably linked to a promoter capable of expressing the first nucleic acid sequence in a host cell, and, linked to the nucleic acid sequence, a cloning site permitting the insertion of a second nucleic acid sequence such that it is capable of being expressed in fusion with the first nucleic acid sequence. Such a vector is a useful vehicle for expressing nucleic acids encoding any desired polypeptide in the form of a fusion protein according to the invention.

A further embodiment of the invention provides host cells transformed or transfected with the vectors for the replication and expression of polynucleotides of the invention. The cells will be chosen to be compatible with the vector and may for example be bacterial, yeast, insect or mammalian.

Such host cells such as prokaryote, yeast and higher eukaryote cells may be used for replicating DNA and producing the fusion protein. Suitable prokaryotes include eubacteria, such as Gram-negative or Gram-positive organisms, such as *E. coli*, e.g. *E. coli* K-12 strains, DH5a and HB101, or Bacilli. Further hosts suitable for fusion protein encoding vectors include eukaryotic microbes such as filamentous fungi or yeast, e.g. *Saccharomyces cerevisiae*. Higher eukaryotic cells include insect and vertebrate cells, particularly mammalian cells. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of fusion protein-encoding nucleic acid to form the fusion protein. The precise amounts of DNA encoding the fusion protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the fusion protein encoded by the DNA is expressed. The composition of suitable media is known to those in the art, so that they can be readily prepared. Suitable culturing media are also commercially available.

Microorganisms, and especially bacteria such as *Escherichia coli*, are among the most successful vehicles for overexpression of both prokaryotic and eukaryotic proteins (for reviews see Hockney, 1994; Grisshammer & Tate, 1995). Accordingly, host cells according to the invention includes microorganisms transformed with vectors encoding fusion proteins according to the invention. However, expression systems employed to express many prokaryotic proteins, including membrane proteins, some cytoplasmic proteins (Dong et al., 1995) and cell division proteins (de Boer et al., 1988; Gutzman et al., 1992) as well as the expression of toxic proteins such as DNAse (Doherty et al., 1993) can in certain circumstances be toxic to the host bacterium.

The expression of eukaryotic proteins in microorganisms can be equally problematical. Over expression of such proteins can also be toxic to the cell. Nonetheless, bacterial expression systems are used in industry and have been used to express a wide variety of proteins, including chymosin, insulin, interferons, insulin-like growth factors, antibodies including humanised antibodies, or fragments thereof.

We have found that by recovering cells from a culture of host cells transformed with an expression vector encoding a fusion protein according to the invention following induction of the gene encoding the fusion protein such that a toxic effect is observable in the host, and cultivating such cells under selective conditions, it is possible to recover from the culture cells which are capable of expressing high levels of the fusion protein without the deleterious effects on the cells normally observed. Surprisingly, the effect observed is general, in that it is observed whatever the target polypeptide which is encoded by the expression system. The cells are thus "resistant to expression system toxicity", as opposed to being resistant to the expression of a particular toxic gene.

Thus, in a preferred aspect, the invention provides a method for improving an expression system comprising the steps of:

(a) preparing an expression system consisting essentially of a host cell transformed with an inducible expression vector encoding a fusion polypeptide according to the invention and a selectable marker;

(b) culturing cells transformed with the expression system under selection pressure compatible with the selectable marker;

(c) inducing the expression system to produce the fusion polypeptide, such that a toxic effect is observable in the host;

(d) recovering host cells from the culture and growing them under a selection pressure and inducing conditions; and (e) selecting viable host cells which continue to produce the fusion polypeptide.

The generation of mutants resistant to expression system toxicity is disclosed in UK patent application 9614700.4 filed on Jul. 12, 1996 in the name of the present applicant and its contents are incorporated herein by reference.

The fusion polypeptide is a fusion protein according to the invention, comprising a first region comprising the sequence of the C-terminal 40 amino acids of bovine $IF_1$ ATPase inhibitor and a further region encoding a desired protein product. Examples of such desired proteins include bovine oxoglutarate-malate carrier, ADP/ATP translocase, rat uncoupling proteins UCP1 and UCP?, *Escherichia coli* unc I, *E. coli* F-ATPase subunit a, bovine F-ATPase subunit epsilon and human immuno-defficiency virus TAT protein.

Preferred bacterial hosts which may be used in the above method include B strains of *E. coli* such as BL21 or a K strain such as JM109. These strains are widely available in the art from academic and/or commercial sources. The B strains are deficient in the Ion protease and other strains with this genotype may also be used. Preferably the strain should not be defective in recombination genes.

Most preferably the strain is BL21(DE3), as disclosed in Studier et al. (1990). Bacteria obtainable by the above selection method, optionally cured of the vector, may also be used as host cells in the present invention. Particular bacteria include *E. coli* C43 (DE3) (deposited at the European Collection of Cell Cultures (ECCC), Salisbury, Wiltshire, UK on Jul. 4, 1996 asB96070445); *E. coli* C0214(DE3) (deposited at the National Collections of Industrial and Marine Bacteria on Jun. 25, 1997 as NCIMB 40884); *E. coli* DK8(DE3)S (deposited at the National Collections of Industrial and Marine Bacteria on Jun. 25, 1997 as NCIMB 40885); or *E. coli* C41(DE3) (deposited at the ECCC on Jul. 4, 1996 as B96070444). Such bacteria, when cured, provide a host for the expression of fusion proteins of the invention and are especially suitable for the expression of fusion proteins whose expression is toxic to bacteria.

F. Selection Method

Although the above-described selection method is fully disclosed in UK patent application 9614700.4, the contents of which are incorporated herein by reference, the method is preferably carried out as follows:

Cultivation of the host cells will take place in the presence of selection pressure, usually in the presence of an antibiotic which is metabolised by the selectable marker gene of the vector. The concentration of antibiotic used will depend upon the exact nature of the resistance gene and the concentration at which untransformed cells are killed by the antibiotic. In the case of ampicillin, somewhere between 20 and 200 $\mu$g per ml of culture will usually be sufficient, although this may be determined empirically if need be by those of skill in the art. In general, suitable concentrations of antibiotics may be determined by reference to standard laboratory reference books (e.g. Sambrook et al, 1989).

Because of the toxicity to the cell of the expression system, the hosts initially will be cultivated under conditions where little or no expression of the target gene occurs so that log phase growth of the cells are achieved. For *E. coli* this will typically mean that the cells are grown to a density of around $10^6$ cells per ml, for example in the range of from $10^2$ to $10^7$ per ml. The cell density may be measured using optical density measurements. Alternatively, the cells may be grown for a suitable period of time, e.g. from 1 to 6, e.g. from 3 to 4 hours at 37° C.

The cells may also be cultured at a lower or higher temperature. This may be useful where for example the expression of the target polypeptide is linked to a temperature-sensitive gene. In such a situation the cells would first be grown at the non-permissive temperature, i.e. the temperature where expression of the target gene does not occur.

Following the culturing of the cells under selection pressure the culture will be induced to express the target gene. A number of inducible promoters operable in bacteria are available. Some promoters, such as the trpE promoter, are inducible by the presence or absence of metabolites or catabolites in the media (namely tryptophan in the case of the trpE promoter). Other promoters include the tac promoter or the lambda PR promoter.

A preferred promoter is however a bacteriophage promoter which requires a bacteriophage polymerase for expression. As mentioned above, a preferred promoter is the T7 promoter which may be used in conjunction with a cell in which the T7 polymerase gene has been cloned and placed under the control of a separate inducible promoter. The T7 polymerase is selective for its promoter binding site and is thus particularly useful since in the absence of T7 polymerase little expression of the target gene will occur. The gene encoding the polymerase is introduced into the cell in a lambda phage and is situated in the phage genome within the int gene so that the phage needs a helper phage for integration or excision from the genome. The polymerase gene is linked to the UV5 promoter which is inducible by isopropyl-β-D-thiogalactopyranoside (IPTG) so that addition of IPTG to the culture induces the production of T7 polymerase. Alternatively the gene may be introduced on a lambda phage by infection with an int⁻ phage such the CE6 phage which is commercially available (Novagen, Madison, USA).

Following induction of the gene encoding the fusion polypeptide, toxic effects on the cell will be observed, and the culture should be maintained for a suitable period of time such that cell death starts to occur, and cells in the culture start to loose the vector encoding the target polypeptide. Usually the cells should be maintained in liquid culture until no more than 50% and preferably no more than 10%, e.g. 1% or 0.1% of cells retain the vector. This may be determined by plating duplicate aliquots of the culture on solid medium with and without the selection pressure and determining the ratio between the number of colonies which grow under selective and non-selective conditions.

Following growth and induction, the cells of the culture are recovered and grown on fresh medium under selection and inducing conditions. The fresh medium is desirably a solid medium, typically agar which contains the necessary nutrients for cell growth. Survivors are examined for the presence of the target gene. We have surprisingly found that some of the colonies recovered from this medium contain cells which are resistant to the toxic effects of the target gene. This is in contrast to normal practice in the art which has regarded the "spent" culture as a waste product following recovery of the target polypeptide.

G. Production of Fusion Proteins and their Processing

Host cells of the invention may be cultured under conditions in which expression of the fusion protein occurs. The fusion protein may be recovered by any suitable means, for example affinity chromatography or HPLC. Where small fusion proteins are involved HPLC is particularly suitable.

The fusion protein may be cleaved, e.g. using an appropriate protease, to provide the polypeptide sequence of interest and this sequence may be recovered from the resulting mixture of first and second regions of the fusion protein.

Alternatively the fusion protein may find application as such, for example as an immunogen where it may form aggregates. This avoids the necessity for preparing immunogenic material form small proteins and peptides by coupling them by separate chemical reaction to a carrier protein such as key-hole limpet hemocyanin (KLH).

H. Production of Antibodies

Fusion proteins according to the invention may be used directly as immunogens, without the use of further adjuvants, to generate antisera and monoclonal antibodies.

In accordance with yet another embodiment of the present invention, there are provided antibodies specifically recognising and binding the fusion proteins according to the invention. More preferably, however, the antibodies are specific for the second region of the fusion proteins, that is the polypeptide which is fused to the gene product of the invention in order to achieve expression thereof. Advantageously, the second region of the fusion protein is recognised by the antibodies when in its natural context. Thus, where the second region is an isolated peptide or domain from a larger protein, that peptide or domain is recognised by the antibodies of the invention in the context of the whole of the larger protein.

The invention moreover provides a method for preparing an immunoglobulin, comprising the steps of:
a) immunising an animal with a fusion protein according to any one of claims 1 to 7: and
b) recovering immunoglobulin specific for a region of the fusion protein from the serum of the animal.

The antibodies (or immunoglobulins) may be isolated in the form of a crude preparation, i.e. an antiserum, by affinity chromatography against the fusion protein or the protein from which one region of the fusion protein is derived. Advantageously, this region is the second region. Alternatively, where the antibody recognises both the C-terminal IF-1 sequence and the fused protein, it may be isolated using a different fusion between the fused protein and a different fusion partner.

The animals used for antibody production may be any animals normally employed for the purpose, particularly mammals. Especially indicated are mice, rats, guinea pigs and rabbits.

In the following description, both antibodies directed to the fusion protein and antibodies raised against the fusion protein which are specific for the one region thereof are referred to as "anti-fusion protein" antibodies.

Antibodies according to the invention may be whole antibodies of natural classes, such as IgE and IgM antibodies, but are preferably IgG antibodies. Moreover, the invention includes antibody fragments, such as Fab, F(ab')2, Fv and ScFv. Small fragments, such Fv and ScFv, possess advantageous properties for diagnostic and therapeutic applications on account of their small size and consequent superior tissue distribution.

The antibodies according to the invention are especially indicated for diagnostic and therapeutic applications. Accordingly, they may be altered antibodies comprising an effector protein such as a toxin or a label. Especially preferred are labels which allow the imaging of the distribution of the antibody in a tumour in vivo. Such labels may be radioactive labels or radioopaque labels, such as metal particles, which are readily visualisable within the body of a patient. Moreover, the may be fluorescent labels or other labels which are visualisable on tissue samples removed from patients.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification. Alternatively, human antibodies may be synthesised using phage display selection techniques.

Antibodies according to the invention may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antibodies, preferentially by immunofluorescent staining of cells expressing the fusion protein, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or immuno-affinity chromatography, e.g. affinity chromatography with the relevant (part of the) fusion protein or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed to the fusion proteins characterised in that a suitable mammal, for example a Balb/c mouse, is immunised with purified fusion protein, or with cells bearing the fusion protein, antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with the fusion protein are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting suitable amounts of fusion protein according to the invention subcutaneously and/or intraperitoneally several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant nucleic acids comprising an insert coding for a heavy chain variable domain and/or for a light chain variable domain of antibodies directed to the fusion proteins of the invention. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed the fusion proteins can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant DNAs comprising an insert coding for a heavy chain murine variable domain of an antibody directed against a fusion protein according to the invention fused to a human y constant domain, for example $\gamma 1$, $\gamma 2$, $\gamma 3$ or $\gamma 4$, preferably $\gamma 1$ or $\gamma 4$. Likewise the invention concerns recombinant DNAs comprising an insert coding for a light chain murine variable domain of an antibody directed to the fusion protein fused to a human constant domain $\kappa$ or $\lambda$, preferably $\kappa$.

In another embodiment the invention pertains to recombinant DNAs coding for a recombinant DNA wherein the heavy chain variable domain and the light chain variable domain are linked by way of a DNA insert coding for a spacer group, optionally comprising a signal sequence facilitating the processing of the antibody in the host cell and/or a DNA coding for a peptide facilitating the purification of the antibody and/or a DNA coding for a cleavage site and/or a DNA coding for a peptide spacer and/or a DNA coding for an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Antibodies and antibody fragments according to the invention are useful in diagnosis and therapy. Accordingly, the invention provides a composition for therapy or diagnosis comprising an antibody according to the invention.

In the case of a diagnostic composition, the antibody is preferably provided together with means for detecting the antibody, which may be enzymatic, fluorescent, radioisotopic or other means. The antibody and the detection means may be provided for simultaneous, simultaneous separate or sequential use, in a diagnostic kit intended for diagnosis.

I. Use in NMR Studies

Fusion proteins according to the invention possess an extremely small fusion partner. One advantage thereof is that the fusion proteins may be employed directly in an NMR experiment without the fusion partner interfering in the spectrum received.

NMR analysis may be performed according to techniques and methododlogy which are known in the art, for example as described in K. Würtrich, "NMR of Proteins and Nucleic Acids". Wiley, New York, 1986, incorporated herein by reference.

The present invention is illustrated with reference to the following examples.

GENERAL PROCEDURES

Over-expression of Proteins and Bacterial Cell Breakage

One freshly transformed colony of the expression host, *E. coli* C41(DE3), is inoculated into 500 ml of 2×TY medium. When the culture has reached an optical density of 0.6 at 600 nm, the expression of the fusion protein is induced by addition of IPTG (0.7 mM final concentration). After induction, the temperature of growth is reduced to 25° C., and the culture is left for 18 hours. Then the cells are harvested by centrifugation. resuspended in TEP buffer (10 mM Tris-HCl, pH 8.0, 1 mM EDTA, and 0.001% phenylmethyl sulphonyl fluoride) and broken by being passed twice through a French pressure cell. The broken cells are centrifuged (60 minutes, 100,000×g).

Purification of Soluble Fusion Proteins on S-Sepharose

If the over-expressed protein is soluble in the bacterial cytosol, the supernatant from the centrifuged broken bacterial cells is applied to a column of S-Sepharose equilibrated in TEP buffer. Proteins bound to the column are eluted with a linear gradient of sodium chloride (0–1M). Most of the fusion proteins elute from the column at a salt concentration of about 0.5 M sodium chloride, except for the If-ADP1 fusion protein, which eluted at about 0.9 M sodium chloride. The purity of the proteins is examined by SDS-PAGE. If impurities remain, appropriate fractions containing the fusion protein are loaded onto a column of Ni-NTA resin (supplied by Quiagen Inc, Chatsworth, Calif.91311, U.S.A. NTA is nitrilo-triacetic acid).

Purification of the Fusion Proteins that Formed Inclusion Bodies

If-epsilon. The pellet resulting from the centrifugation of broken cells of *E. coli* C41(DE3) is redissolved in PBS containing 6M guanidinium hydrochloride and 0.33 M sodium chloride. Insoluble material is removed by centrifugation (40.000 g. 10 min), and the fusion protein is purified from the supernatant either by reverse-phase HPLC or by Ni-NTA column chromatography, as described below.

(a) Reverse-phase HPLC. The solution of If-epsilon is applied to a column of Aquapore RP-300 (Applied Biosystems; 7 micron particle size, 330 Å pore size; 10 cm×2.1 mm internal diameter) equilibrated in 0.1% aqueous trifluoroacetic acid. The column is eluted with a linear gradient of acetonitrile in 0.1% aqueous trifluoroacetic acid (flow rate 0.1 ml/min). The absorbance of the effluent from the column is monitored at 225 nm. The protein eluted from the column at 41% acetonitrile.

(b) Ni-NTA colum chromatography. The sample of If-epsilon dissolved in 6M-guanidine hydrochloride is applied to a column of n Ni-NTA resin (2 ml bed volume). The column is equilibrated in PBS containing 0.33 M sodium chloride. It is washed first with PBS containing 5 mM imidazole (20 ml), and then with PBS containing 50 mM imidazole (20 ml) to elute the If-epsilon. The protein is a detected in the effluent by monitoring the absorbance at 225 nm. The purity of the protein is confirmed by SDS-PAGE.

If-UCP270. This protein (which contains a histidine$_6$ tag at its C-terminal end) is expressed in *E. coli* C41(DE3), where it also forms inclusion bodies in the bacterial cytoplasm. The culture is harvested by centrifugation and the cells are resuspended in PBS buffer containing 0.3 M sodium chloride. Cells are passed twice through a French press, and unbroken cells are eliminated by low speed centrifugation (2,000×g, 10 minutes). Inclusion bodies are collected by centrifugation (10,000 g, 10 minutes). The inclusion body pellet is resuspended in PBS buffer to a protein concentration of 2 mg/ml. Four ml of the suspension are centrifuged (10 minutes, 10,000×g) and the resulting pellet of inclusion bodies is solubilised in buffer A, which contains 0.1 M sodium phosphate, 0.01 Tris-HCl, 8.0 and 6M guanidine hydrochloride. Any remaining insoluble material is removed by centrifugation (10,000×g, 10 minutes). The supernatant is mixed with 2 ml of a slurry of Ni-NTA resin that has been equilibrated in the same buffer. The slurry is stirred at room temperature for 45 minutes, then poured into a 5 ml chromatography column. The column is washed successively with 10 volumes of buffer A, pH 8.0, and 5 volumes of buffer B (8 M urea. 0.1 M sodium phosphate, 0.01 M Tris-HCl, pH 6.8). The fusion protein is eluted by washing the column with 4 ml of buffer C, containing 8M urea, 0.1 M sodium phosphate, 0.01 M Tris, pH 4.5. The detergent lauryl-dimethylamine oxide (LDAO; final concentration 1%) is added to the eluted fractions, and urea is removed by three successive dialysis steps (3 hours each) with the following buffers: first, buffer A, pH 8.0. containing 0.15% LDAO and 4M urea; second,buffer A, pH 8.0, containing 0.15% LDAO and 0.5M urea; third, buffer A, pH 8.0 containing 0.15% LDAO.

Purification of Fusion Proteins on Ni-NTA
Columns after S-Sepharose Chromatography Fractions containing the fusion protein are pooled and incubated 45 minutes at 4° C. with 2 ml of Ni-NTA resin pre-equilibrated with a PBS buffer containing 0.3M sodium chloride. The mixture is then poured into a 10 ml chromatography column and washed with PBS buffer containing 5 mM imidazole (20 ml). Fusion proteins without an additional C-terminal His-tag are eluted with buffer containing 50 mM imidazole and those with an additional C-terminal His-tag with buffer containing 500 mM imidazole. The fusion proteins are dialysed against PBS buffer and concentrated by ultrafiltration with an Amicon column 3.

EXAMPLE 1

Construction of a Fusion Expression Vector

The pMW T7 expression vector (Studier et al., 1990; Way et al., 1990) was adapted to express fusion proteins comprising a fusion partner consisting of amino acids 44 to 84 of $IF_1$. To this end, the amino acid sequence shown in SEQ. ID. No. 1, which consist of amino acids 44 to 84 of $IF_1$ preceded by an initiating ATG (Met), is linked downstream of the T7 promoter in pMW by ligating it at the Nde 1 restriction site therein. Downstream of the $IF_1$ sequence, the cleavable linker G S P K L (SEQ ID NO:8) is inserted, which provides BamHI and HindIII restriction endonuclease sites. This sequence is part of the reverse primer used for vector construction and corresponds to the BamHI and HindIII sites in the vector.

Alternative vectors are constructed in an identical manner, but incorporating alternative cleavable linkers: G S I E G R (SEQ ID NO:9), which is cleavable by Factor Xa, and G S S L V P R G S G S (SEQ ID NO:10), which is cleavable by thrombin.

FIG. 1, lane 1, shows the expression of the fusion partner plus cleavable linker alone. The expression vector is transformed into E. coli C41(DE3) cells (see UK patent application 9614700.4; also Miroux and Walker, 1996). One transformant colony is inoculated into 500 ml 2×TY medium in the presence of ampicillin (100 μg/ml) and grown at 37° C. until the culture has reached an $OD_{600}$ of 0.6. At this stage, fusion partner expression is induced by the addition to the culture of 0.7 mM IPTG. Cells are harvested 16 hours after induction, and lysed in SDS-PAGE solubilisation buffer. The equivalent of 7.5 μl of culture is mixed with an equal volume of SDS-PAGE buffer and loaded, without further purification, onto a 12–22% SDS-PAGE gel. The gel is then stained with coomassie blue 83 dye.

The expressed polypeptide is visible as a major constituent of the total cellular protein in the bacteria.

General Utility Vectors

In order to provide an expression vector which could routinely be used to clone and express a variety of peptides, the vector described above is further modified by the addition of a MCS and a His tag. The His tag facilitates isolation of the fusion protein on a nickel column, although it is not strictly necessary because the IF, 44–84 sequence itself contains 5 His residues.

EXAMPLE 2

Expression of Fusion Proteins

Fusion polypeptides are expressed by cloning nucleic acid sequences encoding amino acids 1 to 39 and 118 to 155 of subunit a of E. coli $F_1F_0$ ATP Synthase, and amino acids 1 to 13 and 55 to 75 of subunit I of E. coli $F_1F_0$ ATP Synthase directly onto the GSPKL (SEQ ID NO:8) extension of the 44–84 sequence of $IF_1$ in the expression vector described in Example 1. The results of the experiment are shown in FIG. 1, lanes 2 to 5.

The expression vectors are transformed into E. coli C41 (DE3). One transformant colony is inoculated into 500 ml 2×TY medium in the presence of ampicillin (100 μg/ml) and grown at 37° C. until the culture has reached an $OD_{600}$ of 0.6. At this stage, fusion partner expression is induced by the addition to the culture of 0.7 mM IPTG. Cells are cultured at the reduced temperature of 25° C. and harvested by centrifugation 18 hours after induction, or 3 hours after induction in the case of the $IF_1$ (44–84)-a(1–39) fusion. The equivalent of 7.5 μl of culture is then loaded, without further purification, onto a 12–22% SDS-PAGE gel. The gel is then stained with coomassie blue 83 dye.

The expressed polypeptides are visible as major constituents of the total cellular protein in the bacteria.

Table 1 shows the results of expression experiments conducted with a number of fusion proteins. In two cases, involving fusions with a portion of the rat mitochondrial uncoupling protein, His-tags were used to further facilitate isolation on nickel columns. Two fusions with the epsilon subunit of bovine $F_1F_0$ ATP synthase were made using alternative cleavable sequences, those for Factor Xa and Thrombin.

In all cases, E. coli C41(DE3) cells were transformed as above and the proteins isolated from the cytosol, other in soluble form or as inclusion bodies as indicated. The inclusion bodies are solubilised either in 6M-guanidium chloride or in 8M-urea and after solubilisation are centrifuged to eliminate membranes and insoluble material. The supernatant conatining the solubilized protein is injected on to a reverse phase HPLC column (C8 Aquapore RP-300, 7 μm particles, 300 Å pore size; 10 cm×2.1 mm internal diameter) that has been equilibrated in 0.1% trifluoroacetic acid and eluted with a linear gradient of acetonitrile. The eluted peptides are detected by monitoring the absorbance of the efluent at 220 nm, and they are analyzed by SDS-PAGE.

In each case, the mass of the fusion protein was calculated by theoretical means and determined experimentally by electro-spray ionisation mass spectrometry with a Perkin-Elmer Sciex API III⁺ triple quadrupole mass spectrometer. The purified protein or peptide sample was dissolved in water or in 0.1% trifluoroacetic acid, and introduced into the inlet stream being sprayed into the instrument. This stream consisted of 50% aqueous acetonitrile. Spectra were recorded in the mass range 10–2,400 (see Methods in Molecular Biology, Volume 61: "Protein and Peptide Analysis by Mass Spectrometry": Edited by J. R. Chapman, Humana Press, 1996; M. Mann and M. Wilm (1995) Trends Biochem Sci. 20, 219–224). The correlation between calculated and determined values is striking, indicating that the polypeptide is entirely undegraded during the synthesis procedure.

TABLE 1

| name | origin, size in aa | sequence | experimental mass | calculated mass | location in C41(DE3) | purification |
|---|---|---|---|---|---|---|
| If | | inhibitor-(44–84)*GSPKL* | | | | |
| If-a1 | m, 39 | If-*GSPKL*-Eca(*1–39*) | 9931.95 | 9933.1994 | IB | reverse phase HPLC |
| If-a3 | m, 38 | If-*GsPKL*-Eca(118–155) | 9444.45 | 9446.9 | IB | reverse phase HPLC |
| If-I1 | m, 13 | If-*GSKNVM*-uncI(*1–13*) | 7010.8 | 7013.00 | IB | reverse phase HPLC |
| If-I2 | m, 21 | If-*GS*-uncI(59–79) | 7561.5 | 7563.5 | IB | reverse phase HPLC |
| If-OGCP1 | M, 19 | If-*GSPKLM*-OGCP(*1–19*) | | | soluble | reverse phase HPLC |
| If-OGCP2 | m, 19 | If-*GSPKL*-OGCP(266–284) | 7771.28 | 7773.87 | IB | reverse phase HPLC |
| If-AAC2 | m, 22 | If-*GSPKL*-AAC(258–279) | 7966.33 | 7969.1 | IB | reverse phase HPLC |
| If-UCP1P1 | m, 14 | If-*GSPKL*-UCP(*1–14*) *EFHHHHHH* | 7970.58 | 7971.86 | soluble | S-Sepharose/Nickel column |
| If-UCP2P1 | m, 13 | If-*GSPKLM*-UCP2(*1–13*) | 6882.32 | 6884.32 | soluble | S-Sepharose/Nickel column |
| If-UCP2P2 | m, 15 | If-*GSPKL*-UCP2(46–60) | 7013.02 | 7014.8 | soluble | S-Sepharose |
| If-UCP2P3 | m, 15 | If-*GSPKL*-UCP2(*101–115*) | 8176.96 | 8178.09 | soluble | S-Sepharose/Nickel column |
| If-UCP270 | m, 69 | If-*GSPKLM*-UCP2(*1–69*) *EFHHHHHH* | | 13801.83 | IB | Nickel column/8 m urea, refolded by dialysis in presence of 0.2% LDAO |
| If-ADPI | g, 37 | If-*GSPKL*-ADPI | 9412.6 | 9410.07 | soluble | S-Sepharose |
| If-Xa-epsilon | g, 50 | If-*GSIEGR*-epsilon | 11,216.06 | 11,217.83 | IB | reverse phase HPLC |
| If-Trb-epsilon | g, 50 | If-*GSSLVPRGSGS*-epsilon | 111,602.42 | 11,603.31 | IB | reverse phase HPLC |
| If-e | g, 70 | If-*GS*-e | 13,298.50 | 13,300.16 | IB | reverse phase HPLC |

Italic letters indicate extra amino-acids, bold letters indicate the name of protein and bold numbers between brackets show the position of the peptide in the protein. The following abbreviations have been used: Inhibitor: bovine inhibitor of the $F_1F_0$-ATP synthase; Eca: subunit a of the *E. coli* $F_1F_0$-ATP synthase; uncI: subunit I of the *E. coli* $F_1F_0$-ATP synthase; OGCP: bovine mitochondrial oxoglutarate carrier; AAC: bovine adenine nucleotide translacator; UCPI: rat mitchondrial Uncoupling protein 1; UCP2: rat mitochondrial Uncoupling protein 2; ADPI: peptide from HIV-TAT protein; epsilon: subunit of the bovine $F_1F_0$-ATP synthase; e: subunit of the bovine $F_1F_0$-ATP synthase; IB: inclusion Bodies; m: membrane protein; g: globular protein; aa: amino-acid; LDAO: lauryl dimethylamine oxide; GSPKL (SEQ ID NO:8): cleavable linker; GSKNVM (SEQ ID NO:11): linker; GS (SEQ ID NO:12): linker; GSPKLM (SEQ ID NO:13): cleavable linker; EFHHHHHH (SEQ ID NO:14): histidine tag; GSIEGR (SEQ ID NO:9): linker cleavable by Factor Xa; GSSLVPRGSGS (SEQ ID NO:10): linker cleavable by thrombin.

Expression of Fusion Peptides

Nucleic cDNA fragments encoding a number of randomly selected peptides were ligated into the expression vectors comprising the $IF_1$ fusion. Expression of these vectors shown in FIG. 2; procedure was identical to the experiments reported in FIG. 1.

The peptides expressed are set forth in Table 2.

TABLE 2

| Peptide Number | Amino Acid Sequence | Length | Stop codon |
|---|---|---|---|
| 1 | GSSLSIWWLLTCIRSPRPWPVKVARWK MRLRTSISAAQRWCAPPPRTIKMSQSW | 54 | Opal |
| 2 | GSGPQPAWRNNKTGTAEWGRINRRLDA INVSGTGSRTAN | 39 | Ochre |
| 3 | GSNCFFSPSSNAHALPCSSLLQ | 22 | Opal |
| 4 | GSPSVMRTRVTR | 12 | Ochre |
| 5 | GSHAHC | 6 | Ochre |
| 6 | GSLSLPFAR | 9 | Ochre |
| 7 | GSLRCFARSRSSGRC | 15 | Ochre |

TABLE 2-continued

| Peptide Number | Amino Acid Sequence | Length | Stop codon |
|---|---|---|---|
| 8 | GSPPRVAATVERH | 13 | Opal |
| 9 | GSCAGCG | 7 | Amber |
| 10 | GSRY | 4 | Ochre |
| 11 | GS | 2 | Opal |
| 12 | GSRTDETYYPAD | 12 | Amber |

EXAMPLE 3

Purification of Fusion Proteins

Nickel Columns

FIG. 5 shows the purification of fusion proteins according to the invention by nickel column and reverse phase HPLC methods. 1/ shows the purification of proteins from inclusion bodies: If-a1 is expressed as inclusion bodies and solubilised using 6M Guanidinium chloride and purified by reverse phase HPLC as for FIG. 3. If-UCP270 fusion protein is solubilised in the presence of urea and purified on a nickel column in the presence of LDAO detergent (see General Procedures for details).

2/ shows the purification of the three fusion proteins If-UCP1P1, If-UCP2P2 and If-UCP3P3 on nickel columns. These fusions are soluble in bacterial cytoplasm and are purified by anion exchange chromatography on S-Sepharose (see General Procedures) followed by affinity chromatography on a nickel column. All protein samples are analysed by SDS-PAGE after purification. The gels are stained with coomassie blue dye 83.

Nickel columns therefore provide convenient and efficient means by which fusion proteins according to the invention may be purified.

Reverse Phase HPLC

FIGS. 3 and 4 illustrate the purification of fusion proteins according to the invention by reverse phase HPLC (see General Procedures; also table 1).

Polypeptides to be isolated by reverse phase HPLC are isolated from bacterial host cells in the form of inclusion bodies and approximately 150 μg of material dissolved in 6M guanidinium hydrochloride in 0.1 M Tris.HCl, pH 8.0. The sample was injected into an Aquapore RP300 column using a HP 1090 Liquid Chromatograph.

The purification of If-I1, If-I2, If-a1 and If-A3 is shown (see also Table 1).

EXAMPLE 4

Generation of Antibodies

A fusion protein comprising amino acids 44 to 84 of $IF_1$ fused, via the linker GSPKL, to residues 1 to 39 of the a subunit of E. coli $F_1F_0$ ATP synthase is used directly for challenge of rabbits in order to generate anti-$F_1F_0$ ATP synthase antibodies.

Immunisation is carried out according to established techniques (See "Antibodies. A Laboratory Manual" by E. Harlow and D. Lane (1988) Cold Spring Harbor, U.S.A.) The purified fusion protein (about 1 mg) was injected into a rabbit in presence of complete Freund's adjuvant. A booster injection of 0.5 mg of the fusion protein in incomplete Freund's adjuvant was made 4 weeks after the initial injection. Antibodies are isolated from rabbit serum and tested for reactivity with the a subunit of $F_1F_0$ ATP synthase. Antibodies capable of selective binding to the chosen polypeptide are obtained by this method.

EXAMPLE 5

Direct Application of Fusion Proteins to NMR

A fusion protein is subjected to NMR analysis according to conventional techniques (K. Würtrich, "NMR of Proteins and Nucleic Acids", Wiley, New York, 1986), but without separating the fusion partner from the polypetide to be analysed.

Proton and $^{13}C$ NMR analysis confirms the structure of the desired protein. The relevant spectra have at most minimal spectral peaks attributable to the fusion partner.

REFERENCES

Ausubel. F. M., Brent, R., Kingston, R. E., Seidman, D. D., Smith, J. G., Struhl. J. A. & Struhl. K. (1987). In *Current Protocols in Molecular Biology*. John Wiley & Sons Inc., New York.

Bertin. B., Freissmuth, M., Breyer, R. M., Schutz, W., Stosberg. A. D., and Marullo, S. (1991). Functional expression of the human serotonin 5-HT1A receptor in *Escherichia coli. J. Biol. Chem.*, 267, 8200–8206.

Chalfie. M., Tu, Y.. Euskirchen, G., Ward, W. W. & Prasher. D. C. (1994). Green fluorescent protein as a marker for gene expression. *Science* 263, 802–805.

Chapot. M. P., Eshdat, Y., Marullo, S., Guillet, J. G., Charbit, A., Strosberg, A. D., Delavier-Klutchko, C. (1990). Localization and characterization of three different beta-adrenergic receptors expressed in *Escherichia coli. Eur J Biochem* 187 (1): 137–144.

Collinson, I. R., van Raaij, M. J., Runswick, M. J., Fearnley, I. M., Skehel, J. M., Orriss, G., Miroux, B. & Walker, J. E. (1994). ATP synthase from bovine heart mitochondria: in vitro assembly of a stalk complex in the presence of $F_1$-ATPase and in its absence. *J. Mol. Biol.* 242, 408421.

de Boer et al., (1983) PNAS (USA) 80:21–25.

de Boer. P. A. J., Crossley, R. E. & Rothfield, L. I. (1988). Isolation and properties of *min B*, a complex genetic locus involved in correct placement of the division site in *Escherichia coli. J. Bact.* 170, 2106–2112.

Doherty, A. J., Connolly, B. A. & Worrall, A. F. (1993). Overproduction of the toxic protein bovine pancreatic DNAse I in *Escherichia coli* using a tightly controlled T7 promoter based vector. *Gene* 136, 337–340.

Dong. H., Nilsson, L. & Kurland, C. G. (1995). Gratuitous overexpression of genes in *Escherichia coli* leads to growth inhibition and ribosome destruction. *J. Bacteriol.* 177, 1497–1504.

Fiermonte, G., Walker, J. E. & Palmieri, F. (1993). Abundant bacterial expression and reconstitution of an intrinsic membrane transport protein from bovine mitochondria. *Biochem. J.* 294, 293–299.

Fillingame, R. H. (1990). Molecular mechanics of ATP synthesis by $F_1F_0$-type $H^+$-transporting ATPases. *The Bacteria* 12, 345–391.

Friedberg, E. C., Walker, G. C. & Siede, W. (1995). *In DNA repair and mutagenesis*. ASM Press. Washington D.C.

George, J. W., Brosh Jr, R. M. & Matson, S. W. (1994). A dominant negative allele of the *Escherichia coli* uvrD gene encoding DNA helicase II. *J. Mol. Biol.* 235, 424–435.

Grisshammer, R. & Tate, C. G. (1995). Overexpression of integral membrane proteins for structural studies. *Qu. Rev. Biophys.* 28, 315–422.

Guzman et al., (1995) J. Bacteriol. 177:4121–4130.

Guzman, L. M., Barondess, J. J. & Beckwith, J. (1992). Fts L, an essential cytoplasmic membrane protein involved in cell division in *Escherichia coli. J. Bacteriol.* 174, 7716–7728.

Hockney, R. C. (1994). Recent developments in heterologous protein production in *Escherichia coli. Trends Biotechnol.* 12, 456–463.

Iost, I. & Dreyfus, M. (1995). The stability of *Escherichia coli* lacZ mRNA depends upon the simultaneity of its synthesis and translation. *EMBO J.* 14, 3252–3261.

Kamata. H., Akiyama, S., Morosawa, H., Ohta, T., Hamamoto, T., Kambe, T., Kagawa, Y. & Hirata, H. (1992). Primary structure of the alanine carrier protein of thermophilic bacterium PS3. *J. Biol. Chem.* 267, 21650–21655.

Kane, J. F. (1995). Effects of rare codon clusters on high-level expression of heterologous proteins in *Escherichia coli. Curr. Opinion Biotechnol.* 6, 494–500.

Kiefer. H., J. Krieger, J. D. Olszewski, G. Von Heijne, G. D. Prestwich, and H. Breer. (1996). Expression of an olfactory receptor in *Escherichia coli*: purification, reconstitution, and ligand binding. *Biochemistry* 35:16077–16084.

Laemmli, U. K. (1970). Cleavage of structural proteins during the assembly of the head of bacteriophage T4. *Nature* 227, 680–685.

Makarova, O. V., Makarov, E. M., Sousa, R. & Dreyfus, M. (1995). Transcribing of *Escherichia coli* genes with mutant T7 RNA polymerases: Stability of lacZ mRNA inversely correlates with polymerase speed. *Proc. Natl. Acad. Sci. U.S.A.* 92, 12250–12254.

Moffatt, B. A. & Studier, F. W. (1987). T7 lysozyme inhibits transcription by T7 RNA polymerase. *Cell* 49, 221–227.

Murli, S. & Walker, G. C. (1993). SOS mutagenesis. *Current Opinion Genetics and Development* 3, 719–725.

Orriss. G. L., Runswick, M. J., Collinson, I. R., Miroux, B., Fearnley , I. M.. Skehel, J. M. & Walker, J. E. (1996). The δ- and ε-subunits of bovine $F_1$-ATPase interact to form a heterodimeric subcomplex. *Biochem. J.* 314, 695–700.

Runswick, M. J., Powell, S. J., Nyren, P. & Walker, J. E. (1987). Sequence of the bovine mitochondrial phosphate carrier protein: structural relationship to ADP/ATP translocase and the brown fat mitochondrial uncoupling protein. *EMBO J.* 6, 1367–1373.

St. Johnston, D., Beuchle, D. &. Nüsslein-Volhard, C. (1991). *Staufen*, a gene required to localise maternal RNAs in the *Drosophila* egg. *Cell* 66, 51–63.

Studier, F. W., Rosenberg, A. H., Dunn, J. J. & Dubendorff, J. W. (1990). Use of T7 RNA polymerase to direct expression of cloned genes. *Methods in Enzymol.* 185, 60–89.

Tucker, J., and Grisshammer R. (1996). Purification of a rat neurotensin receptor expressed in *Escherichia coli*. *Biochem. J.* 317, 891–899.

Uzan. M.. Favre, R. & Brody, E. (1988). A nuclease that cuts specifically in the ribosome binding site some T4 mRNAs. *Proc. Natl. Acad. Sci. U.S.A.* 85, 8895–8899.

Walker. J. E. & Runswick, M. J. (1993). The mitochondrial transport protein super-family. *J. Bioenerget. Biomembranes* 25, 435–467.

Walker, J. E., Runswick, M. J. & Poulter, L. (1987). ATP synthase from bovine mitochondria: characterisation and sequence analysis of two membrane associated subunits and of their corresponding c-DNAs. *J. Mol. Biol.* 197, 89–100.

Way, M., Pope, B., Hawkins, M. & Weeds, A. G. (1990). Identification of a region in segment 1 of gelsolin critical for actin binding. *EMBO J.* 9, 4103–4109.

We claim:

1. A fusion protein comprising:
   a) a first amino acid sequence comprising the sequence of the C-terminal 40 amino acids of bovine $IF_1$ ATPase inhibitor protein, and
   b) a second amino acid sequence not naturally associated with the first amino acid sequence.

2. The fusion protein according to claim 1 which further comprises a cleavable linker region between the first and second amino acid sequences.

3. The fusion protein of claim 1 wherein said first amino acid sequence is at or proximal to the N-terminus of the fusion protein.

4. A fusion protein of claim 1 wherein said second amino acid sequence is 2 to 100 amino acids in length.

5. A fusion protein of claim 1 wherein said second amino acid sequence comprises a mammalian hormone.

6. A fusion protein of claim 1 wherein the first amino acid sequence is 25 to 100 amino acids.

7. A fusion protein of claim 1 wherein the first amino acid sequence comprises the bovine $IF_1$ ATPase inhibitor protein.

8. A fusion protein prepared by a method comprising:
   (i) culturing a host cell comprising an expression vector comprising a nucleic acid encoding the fusion protein of claim 1 under conditions which provide for expression of said fusion protein encoded by the expression vector within the host cell; and
   (ii) recovering the fusion protein.

9. A method for preparing an immunoglobulin, comprising the steps of:
   a) immunizing an animal with the fusion protein of claim 1; and
   b) recovering immunoglobin specific for a region of the fusion protein from the serum of the animal.

* * * * *